United States Patent
Erdman et al.

(10) Patent No.: US 9,204,928 B2
(45) Date of Patent: *Dec. 8, 2015

(54) COUPLER ASSEMBLY FOR CATHETERS

(71) Applicant: St. Jude Medical, Atrial Fibrillation Division, Inc., St. Paul, MN (US)

(72) Inventors: Arthur G. Erdman, New Brighton, MN (US); Saurav Paul, Minneapolis, MN (US); Troy T. Tegg, Elk River, MN (US)

(73) Assignee: St. Jude Medical, Atrial Fibrilation Division, Inc., St. Paul, MN (US)

( * ) Notice: Subject to any disclaimer, the term of this patent is extended or adjusted under 35 U.S.C. 154(b) by 40 days.

This patent is subject to a terminal disclaimer.

(21) Appl. No.: 13/961,435

(22) Filed: Aug. 7, 2013

(65) Prior Publication Data

US 2014/0046194 A1 Feb. 13, 2014

Related U.S. Application Data

(63) Continuation of application No. 12/650,461, filed on Dec. 30, 2009, now Pat. No. 8,515,521.

(60) Provisional application No. 61/142,079, filed on Dec. 31, 2008.

(30) Foreign Application Priority Data

Dec. 30, 2009 (WO) .................. PCT/US2009/06985

(51) Int. Cl.
*A61M 25/00* (2006.01)
*A61B 18/14* (2006.01)
(Continued)

(52) U.S. Cl.
CPC ........... *A61B 18/1492* (2013.01); *A61B 5/0084* (2013.01); *A61B 5/065* (2013.01);
(Continued)

(58) Field of Classification Search
CPC ........... A61B 18/1492; A61B 18/1442; A61B 2019/464; A61B 2019/2211; A61B 2017/00314; A61B 1/0008; A61M 25/0138
See application file for complete search history.

(56) References Cited

U.S. PATENT DOCUMENTS 4,757,194 A 7/1988 Simms
4,834,101 A 5/1989 Collison
(Continued)

FOREIGN PATENT DOCUMENTS

EP 0900549 3/1999
EP 2062545 5/2009
(Continued)

OTHER PUBLICATIONS

Title: Micro Pressure Measurement System—Product Overview Citation: Biopac Systems, Inc. Reference pp. 1-39 Publication Date: Aug. 2007.

(Continued)

*Primary Examiner* — Elmer Chao
(74) *Attorney, Agent, or Firm* — Dykema Gossett PLLC

(57) ABSTRACT

Coupler assemblies and methods are disclosed as the coupler assemblies may be used with a catheter. An exemplary coupler assembly includes a spherical linkage coupler for a catheter. The coupler comprises a first cylinder portion for connecting to a structure, and a second cylinder portion for connecting to a distal end of a body of the catheter. The coupler also comprises a spherical linkage including at least two link arms. Each of the two link arms are connected on one end to the first cylinder portion and on the other end to the second cylinder portion. The two link arms connect a portion of the structure to the distal end of the catheter and enable the structure to move relative to the distal end of the catheter in response to an external force exerted on the structure.

20 Claims, 15 Drawing Sheets

(51) Int. Cl.

| | | |
|---|---|---|
| *A61B 5/00* | (2006.01) | |
| *A61M 25/01* | (2006.01) | |
| *A61B 5/06* | (2006.01) | |
| *A61B 5/107* | (2006.01) | |
| *A61M 39/10* | (2006.01) | |
| *A61B 18/24* | (2006.01) | |
| *A61B 17/00* | (2006.01) | |
| *A61B 19/00* | (2006.01) | |

(52) U.S. Cl.
CPC ............ *A61B 5/1076* (2013.01); *A61B 5/6852* (2013.01); *A61B 5/6885* (2013.01); *A61M 25/0069* (2013.01); *A61M 25/01* (2013.01); *A61M 25/0138* (2013.01); *A61M 39/10* (2013.01); *A61B 18/24* (2013.01); *A61B 2017/00057* (2013.01); *A61B 2017/00084* (2013.01); *A61B 2019/465* (2013.01); *A61M 25/007* (2013.01); *A61M 25/0071* (2013.01); *A61M 25/0141* (2013.01); *A61M 2025/0002* (2013.01)

(56) References Cited

U.S. PATENT DOCUMENTS

| | | |
|---|---|---|
| 5,122,137 A | 6/1992 | Lennox |
| 5,413,107 A | 5/1995 | Oakley |
| 5,460,182 A | 10/1995 | Goodman |
| 5,928,222 A | 7/1999 | Kleinerman |
| 6,113,590 A | 9/2000 | Fischer |
| 6,743,239 B1 | 6/2004 | Kuehn |
| 7,060,965 B2 | 6/2006 | Vidovic |
| 8,048,063 B2 | 11/2011 | Aeby |
| 2002/0123749 A1 | 9/2002 | Jain |
| 2004/0116992 A1 | 6/2004 | Wardle |
| 2005/0245789 A1 | 11/2005 | Smith |
| 2007/0060847 A1 | 3/2007 | Leo |
| 2008/0009750 A1 | 1/2008 | Aeby |
| 2008/0294144 A1 | 11/2008 | Leo |
| 2009/0060977 A1 | 3/2009 | Lamson |
| 2009/0093806 A1 | 4/2009 | Govari |
| 2009/0131931 A1 | 5/2009 | Lee et al. |

FOREIGN PATENT DOCUMENTS

| | | |
|---|---|---|
| WO | 2004/069072 | 8/2004 |
| WO | 2008/137303 | 11/2008 |

OTHER PUBLICATIONS

Title: Fiber Optic Interferometer Fabry-Perot Citation: http://physics.nad.ru/Physics/English/ifp_txt.htm Reference pp. 1-5 Publication Date: Oct. 15, 2007.

Title: General Pharmacology Samba—Blood Pressure Systems Citation: http://www.bioseb.com/bioseb/anglais/default/item id=94 cat id=3 Samba%20-%20Pressure%20System.php Reference pp. 1-4 Publication Date: Oct. 2007.

Title: The Samba Technology Citation: Samba Sensors: www.samba.se/index2.cfm?PageID=45 Publication Date: Oct. 2007.

Author: Samba Sensors Title: Publications related to Samba Sensors AB Reference pp. 1-3 Publication Date: unknown.

Author: Grace, Daniel Title: High-Tech Partnership Bundles Catheters with Fiber-Optic Sensors Citation: Medical Product Manufacturing News Publication Date: Sep. 2007.

Title: International Search Report & Written Opinion Citation: PCT/US2009/069857 Publication Date: Mar. 2, 2010.

Title: Supplementary European Search Report Citation: EP 08746501 Publication Date: Jul. 2, 2012.

Author: Peirs, J. Title: Design of an Optical Force Sensor for Force Feedback during Minimally Invasive Robotic Surgery Citation: Katholieke Universiteit Leuven, Leuven Belgium; www.mech.kuleuven.ac.be Reference pp. 1-4 Publication Date: 2003.

Title: Supplementary European Search Report Citation: EP 09837175 Publication Date: Apr. 3, 2013.

Title: International Search Report and Written Opinion Citation: PCT/US2008/061092 Publication Date: Sep. 3, 2008.

COUPLER ASSEMBLY FOR CATHETERS

CROSS-REFERENCE TO RELATED APPLICATIONS

This application is a continuation of U.S. patent application Ser. No. 12/650,461, filed 30 Dec. 2009, (the '461 application), which claims priority to and the benefit of U.S. provisional application No. 61/142,079 filed 31 Dec. 2008 (the '079 application) and international patent application number PCT/US09/69857 (the '857 application) filed 30 Dec. 2009. The entire contents of the '461 application, the '079 application, and the '857 application are hereby incorporated by reference as though fully set forth herein.

BACKGROUND OF THE INVENTION a. Field of the Invention

The instant invention relates to a coupler assembly for catheters having force-sensing capabilities. The instant invention includes a mechanical coupler for coupling a catheter shaft and distal tip sensing components. Such a system may be used with catheters for visualization, mapping, ablation, and/or other methods of diagnosis and treatment of tissue. The instant invention also relates to a method for using a mechanical coupler to couple a catheter shaft and distal tip components, for medical or non-medical purposes.

b. Background Art

The visualization and treatment of organs and tissues has been advanced through the increasing use of catheter systems. Catheter systems have been designed for the incorporation of various components to treat and diagnose ailments, as accomplished through the mapping of organs, sensing of thermal and electrical changes exhibited by a tissue (e.g., heart), as well as the application of energizing sources (such as radiofrequency, cryogenics, laser, and high frequency ultrasound) to tissue.

Catheter systems generally include a portion that contacts the tissue or organ, or is inserted in an environment (e.g., heart chamber or vessel) to detect a number of parameters, such as for example, location of the tissue, contact or pressure exerted on the tissue, electrophysiological attributes of the tissue, or other type of parameters that aid in the evaluation or treatment of the organ or tissue.

It is known that sufficient contact between a catheter, in particular an electrode provided in connection with a catheter, and tissue during a procedure is generally necessary to ensure that the procedures are effective and safe. Current techniques of mapping, visualization and treatment using energizing sources, such as the use of radiofrequency energy during ablation, rely on placing of the electrode (or another component) of a catheter system in consistent mechanical contact with targeted tissue. Perforation of the cardiac wall as well as lesion formation (such as lesions created by exposure to radiofrequency) partially depends upon the direction of contact between the electrode and tissue. In particular, for endocardial catheter applications, the point of electrode-tissue contact is typically 150 cm away from the point of application of force applied by the operator (whether manual or automated) of the catheter outside of the body. Coupled with the fact that a beating heart is a dynamically moving wall, this gives rise to some functional and theoretical challenges such as ensuring that the electrode is in sufficiently constant mechanical contact with the myocardial wall.

Catheter systems having sensor assemblies, such as those mounted on the catheter shaft proximal to the electrode (or another component) or remotely in the handle set, leave the possibility, however small, of obtaining false positive outcomes when detecting contact between the electrode and the tissue. False positive outcomes may occur, for example, when the distal portion of the catheter, and not the electrode, is in contact with the tissue. Such condition may arise during the catheter manipulation in the heart when, for instance, the distal portion of the catheter is curled inward so much as to lose electrode contact with the tissue, while the distal portion of the catheter is in contact with the tissue. When that happens, remotely placed sensors can generate signals due to the deflection of the catheter shaft, thereby falsely indicating contact between the electrode and tissue. Accordingly, contact sensors coupled to the electrode and provided in the distal tip of the catheter can, among other things, help reduce the possibility of obtaining false positive outcomes when detecting contact between the electrode (or another component) and the tissue.

Force sensor configurations that address the foregoing issues have been previously disclosed. In some embodiments, such force sensors include a coupler that couples the electrode with the catheter shaft. In those cases, the sensitivity and the dynamic range of the force sensor depend upon the stiffness of the coupler. Furthermore, the sensitivity and the dynamic range depends upon the directional stiffness of the coupler range of the force sensor because force is a vector (i.e. force has a magnitude and direction). Thus, for example, if the coupler is stiffer in the axial direction than in the transverse direction, the force sensor will have a wider dynamic range in the axial direction than in the transverse direction, and will be more sensitive in the transverse direction than in the axial direction.

BRIEF SUMMARY OF INVENTION

For some applications, it is desirable to have a catheter system that includes distal tip sensors that detect changes in an interactive surface provided by an electrode (or another structure). It is also desirable to provide a system which is insensitive to radiofrequency (RF) field, electromagnetic interference (EMI), and thermal effects. Furthermore, it is also desirable to have a system which minimizes false positives, is robust in construction and has a wide dynamic range. In an embodiment, the electrode may be subjected to a compressive force due to mechanical contact of the electrode surface with another body or surface. The sensors coupled to the distal tip of the catheter using the coupler assembly of the invention can be used to measure contact of an electrode with a dynamically moving wall, such as a beating heart.

Coupler assemblies and methods are disclosed as the coupler assemblies may be used with a catheter. In one embodiment, a coupler assembly includes a spherical linkage coupler or spherical linkage for a catheter. The coupler comprises a first cylinder portion for connecting to a structure, and a second cylinder portion for connecting to a distal end of a body of the catheter. The coupler also comprises a spherical linkage including at least two link arms. Each of the two link arms are connected on one end to the first cylinder portion and on the other end to the second cylinder portion. The two link arms connect a portion of the structure to the distal end of the catheter and enable the structure to move relative to the distal end of the catheter in response to an external force exerted on the structure.

In another embodiment, a catheter system comprises a body having a proximal end and a distal end, and a structure. The structure includes a tip portion and a base portion, and a generally central axis. A coupler assembly is provided for connecting a portion of the structure to the distal end of the catheter. The coupler assembly comprises a first cylinder portion and a second cylinder portion. The coupler assembly also comprises a spherical linkage including two link arms. Each of the two link arms connected on one end to the first cylinder portion and on the other end to the second cylinder portion.

For the coupler assembly described above, in an embodiment, the distal end of the catheter may include a coupling member having a neck portion. The neck portion of the coupling member, in an embodiment, may move relative to an external force exerted on the structure. In an embodiment, the neck portion of the coupling member may include a twist, torsion bar, alpha, dove-tail or spring shaped elastic portion for enabling external axial and transverse forces and torques exerted on the structure to be sensed by the sensor. The coupling member, in an embodiment, may include a mounting shaft that defines an internal recessed groove for receiving at least a portion of the sensor. In an embodiment, the tip portion of the structure may include an irrigation port. The structure, in an embodiment, may include a lumen provided within an internal cavity of the structure, with the lumen being positioned adjacent to the base and tip portions of the structure.

For the coupler assembly described above, in an embodiment, a lumen may be disposed within the body of the catheter, with at least a portion of the lumen extending into the structure for slidably receiving one or more sensing components. In an embodiment, a lumen may be disposed within the body of the catheter, with at least a portion of the lumen extending into the structure for slidably receiving one or more energizing components. The energizing component may be a radiofrequency current, direct current, high-intensity ultrasound, laser, cyrogenic, chemical, electromagnetic radiation, and combinations thereof. In an embodiment, the tip portion of the structure may include a portion configured to perform ablation. The sensor, in an embodiment, may be adapted to measure a parameter, such as, intensity, wavelength, phase, spectrum, speed, optical path, interference, transmission, absorption, reflection, refraction, diffraction, polarization, and/or scattering. The coupler may also be used in conjunction with other sensors such as, electromechanical sensors, magnetic sensors, resistive sensors, inductive sensors, capacitive sensors, and quantum sensors, to name only a few examples.

In another embodiment, a method for sensing contact force in a catheter is disclosed. The method comprises connecting a first cylinder portion to a structure, and connecting a second cylinder portion to a distal end of a body of the catheter. A spherical linkage is provided to connect the first cylinder portion to the second cylinder portion so that the structure moves relative to the distal end of the body of the catheter in response to an external force exerted on the structure. A sensor is provided for the structure, the sensor sensing changes in intensity of a signal from the sensor responsive to displacement associated with the structure in response to the contact force exerted by the structure on a tissue.

For the method described above, in an embodiment, the structure may perform RF ablation, HIFU ablation, laser ablation, cryogenic ablation, chemical ablation, radiation therapy, ultrasonic imaging, electrical pacing, EP pacing, electrical sensing, and/or EP sensing. In an embodiment, the sensed contact force may be utilized for automatically limiting a maximum contact force, warning of a high or unacceptable contact force, giving visual or audible feedback to a practitioner regarding a tissue contact force, warning of a loss of contact force or contact, and/or warning of a contact force which may be too low.

The foregoing and other aspects, features, details, utilities, and advantages of the invention will be apparent from reading the following description and claims, and from reviewing the accompanying drawings.

DETAILED DESCRIPTION OF THE INVENTION

Figure 1:
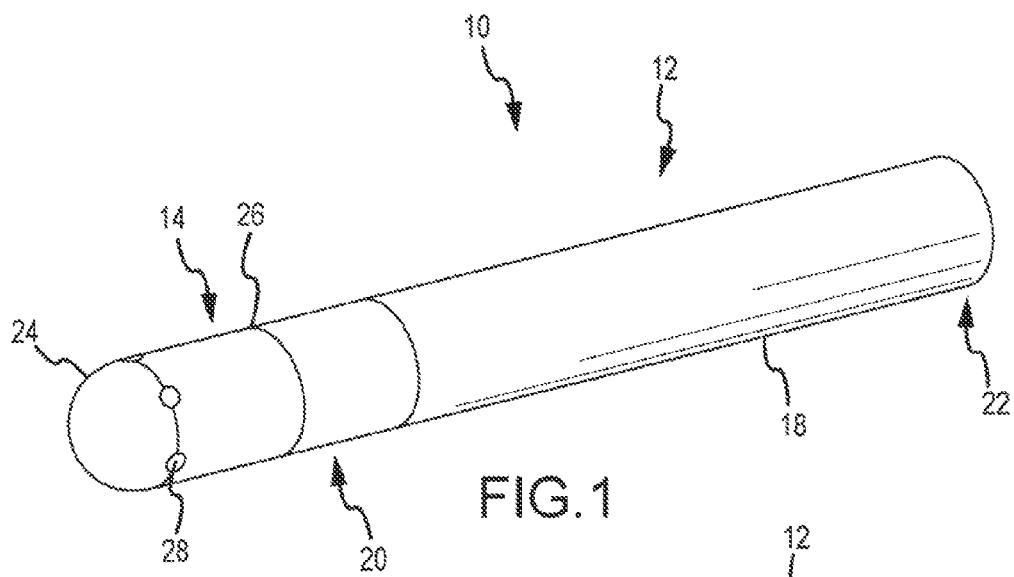
FIG. 1 is a partial perspective view of a catheter assembly in accordance with an embodiment of the invention.
Figure 2:
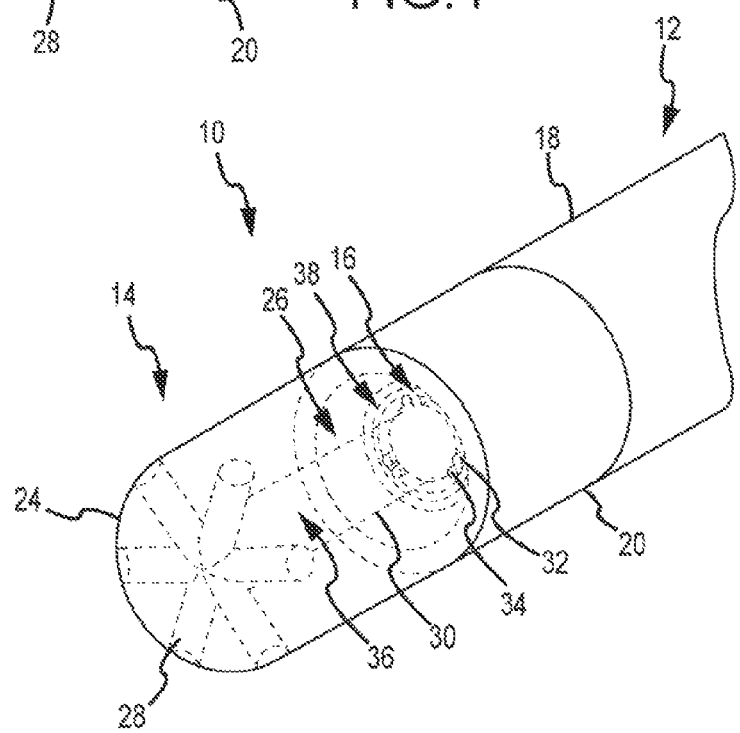
FIG. 2 is an enlarged partial perspective view of the catheter assembly shown in FIG. 1, wherein the electrode and portion of the sensing assembly is shown in phantom.

Referring now to the drawings wherein like reference numerals are used to identify like components in the various views, FIGS. 1 and 2 illustrate an exemplary embodiment of a contact sensing assembly 10 which may implement a coupler assembly 50 of the invention (see, e.g., FIGS. 3A-D). In a general form, the contact sensing assembly 10 includes a catheter 12, an electrode 14 connected to the catheter 12, and a sensor 16 for interacting with a portion of electrode 14. The contact sensing assembly 10 may be used in the diagnosis, visualization, and/or treatment of tissue (such as endocardial tissue) in a body. Contact sensing assembly 10 may be used in a number of diagnostic and therapeutic applications, such as for example, the recording of electrograms in the heart, the performance of cardiac ablation procedures, and/or various other applications. The catheter 12 can be used in connection with a number of applications that involve humans, or other mammals, for tissue observation, treatment, repair or other procedures. Moreover, the invention is not limited to one particular application, but rather may be employed by those of ordinary skill in the art in any number of diagnostic and therapeutic applications. For example, the catheters disclosed herein may be usable in combination with a robotic system (e.g., disclosed in commonly owned and copending applications titled "Robotic Catheter System," "Robotic Catheter Manipulator Assembly," "Robotic Catheter Device Cartridge," "Robotic Catheter Rotatable Device Cartridge," "Robotic Catheter Input Device," "Robotic Catheter System Including Haptic Feedback," and "Robotic Catheter System with Dynamic Response," the respective disclosures of which are incorporated herein by reference in their entirety), for example, for coupling to a computer controlled catheter or surgical instrument for real-time feedback and precise control during a procedure.

Catheter 12 of the invention includes a body 18 having a distal end 20 and a proximal end 22. Body 18 of catheter 12 is generally tubular in shape, although other configurations of the catheter 12 may be used as known in the industry. Distal end 20 of catheter 12 is connected to electrode 14, while body 18 of catheter 12 may house sensor 16 and other components used in the diagnosis and/or treatment of tissue. If desired, the outer portion of catheter 12 may have a braided outer covering therein providing increased flexibility and strength. The catheters of the invention vary in length and are attached to a handle or other type of control member that allows a surgeon or operator of the catheter 12 to manipulate the relative position of the catheter 12 within the body from a remote location, as recognized by one of ordinary skill in the art.

As generally shown in FIG. 1, an embodiment of the invention includes distal end 20 of catheter 12 that includes at least a portion or segment that exhibits increased flexibility relative to more proximal portions of the catheter 12. The increased flexibility of at least a portion or segment associated with the distal end 20 may be achieved using the coupler assembly 50 of the present invention (see, e.g., FIGS. 3A-D), which allows for increased flexibility at a portion or segment of the distal end 20 of catheter 12.

Electrode 14 is connected to distal end 20 of catheter 12 by the coupler assembly 50 (see, e.g., FIGS. 3A-D). Upon the exertion of external contact force on the surface of electrode 14, at least a portion of distal end 20 of catheter 12 flexes and/or bends and/or compresses relative to electrode 14 (see, e.g., FIGS. 8A-B). The relative movement (e.g., displacement either axially, laterally, compression, or a combination thereof) of distal end 20 may be proportionate or correlated to the force exerted on electrode 14. The coupler assembly 50 will be described in more detail below with reference to the remaining figures.

Electrode 14 includes a tip portion 24 and a base portion 26. Electrode 14 may be configured to include a means for irrigating. For example, without limitation, the incorporation of at least one irrigation port 28 within electrode 14, therein providing an irrigated electrode tip. An irrigated electrode tip allows for the cooling of electrode 14, for instance, through the transporting of fluid through electrode 14 and around the surface of the tissue. A number of different types of electrodes, irrigated and non-irrigated, may be connected and incorporated for use with an electrode 14 according to embodiments of the invention depending on the type of procedures being done. Such irrigated electrodes include, but are not limited to, those disclosed in U.S. patent application Ser. No. 11/434,220 (filed May 16, 2006), Ser. No. 10/595,608 (filed Apr. 28, 2006), Ser. No. 11/646,270 (filed Dec. 28, 2006) Ser. No. 11/647,346 (filed Dec. 29, 2006) and 60/828, 955 (filed Oct. 10, 2006), each of which is hereby incorporated by reference as though fully set forth herein.

The catheter 12 may also include a sensing system. In one exemplary embodiment where an optical sensor is implemented, electrode 14 may include an optically interactive surface 30 on a portion of the electrode 14 that interacts with the optical sensor 16. As shown in FIG. 2, electrode 14 may further include an electrode cavity 36, as shown in phantom. Electrode cavity 36 may also be used to provide a number of different components and/or functions in connection with the electrode. In an embodiment, electrode cavity 36 may further provide the optically interactive surface 30 therein enabling an optical sensor 16 to interact with the internal surface of electrode 14 provided by electrode cavity 36. In alternate embodiments, electrode cavity 36 may serve as a lumen for transferring of irrigation channels, electrical components, or any other type assembly components transferred through electrode 14.

In general, an optically interactive surface 30 may be provided on or in connection with a surface associated with electrode 14, such that the surface positioning, configuration, and orientation of the interactive surface 30 (which has a know position with respect to the electrode) allows sufficient interaction and/or functional communication with the optical sensor 16 such that a change in the communication (e.g., optical signal, light intensity) can provide a means for determining the contact force and/or orientation of the electrode with the tissue or surrounding area.

The optical sensor 16 may be positioned within the distal end 20 of the catheter 12. The optical sensor 16 may include at least one optic fiber that transmits and receives an optical signal, such as light energy. The optical sensor 16 may also be manufactured to transmit and/or receive various types of signals including those associated with electromagnetic radiation, lasers, x-rays, radiofrequency, etc. In an embodiment, optical sensor 16 may use light energy to determine the relative contact (e.g., force, stress, and/or orientation) between electrode 14 and an external surface in operational contact with the electrode—for example, tissues and surrounding environments, including organs, heart chambers, and interior of vessels. In an embodiment, the optical sensor may be adapted to measure one or more parameters, including, for example, intensity, wavelength, phase, spectrum, speed, optical path, interference, transmission, absorption, reflection, refraction, diffraction, polarization, and scattering.

In an embodiment, one or more force vectors may be used to determine the contact force and/or orientation of the electrode in connection with the surrounding tissue or other external surfaces. In order to determine light or optical intensity, optical sensor includes a receiver and an emitter for receiving and emitting light energy, respectively. The receiver and emitter may be included in a single fiber optic cable or in two separate fiber optic cables, such as shown in FIG. 2. A number of optical sensors may be arranged within distal end 20 of catheter 12 to operatively (e.g., optically) interact with an interactive surface that is provided in connection with electrode 14. Moreover, a number of receivers and emitters may be disposed within distal end 20 of catheter 12 in various configurations and combinations to assess contact and/or orientation readings. Such positioning and combinations can be configured adapted to optimize their operation for an intended application or environment.

Exemplary embodiments of an optical sensor for use with catheters, such as the catheter 10, are described in more detail in the '857 Application. Therefore, further discussion is not necessary herein in order to fully practice the present invention. It should be noted, however, that the optical sensor described above is discussed for purposes of illustration only and is merely one type of sensor that may be implemented with the present invention. Other types of sensors may also be implemented, including but not limited to, capacitive, inductive, magnetic, electromagnetic, acoustic, piezoelectric, pressure, stress, strain, Wheatstone bridge-type, motion, resistive, and other types of sensors now known or later developed.

It is noted that at least one lumen is included in the catheter 12 for receiving various energizing or sensing components. Exemplary sensing components may include a thermal sensor, pressure sensor, tissue sensor, electrogram sensor, or other type of sensors and combinations thereof that are known by those of ordinary skill in the art. An additional lumen may extend from catheter 12 through coupler assembly 50 and into electrode 14, therein providing an energizing component, such as source for radiofrequency current, direct current, high-intensity ultrasound, laser, cryogenics, or other type of energizing component and combinations that are known by those of ordinary skill in the art. Additional lumens may also be provided by assembly 10 for communication with additional components for the assembly, such as electrical components, fluid (i.e. saline) passageways, or others known in the industry.

It is also noted that electrode 14 may have alternate tip configurations depending on the type of procedure or use of the catheter 12. As previously suggested, electrode 14 may be provided having an irrigated electrode tip or a non-irrigated electrode tip. Each of these may be used in connection with embodiments of the invention.

Figure 8A:
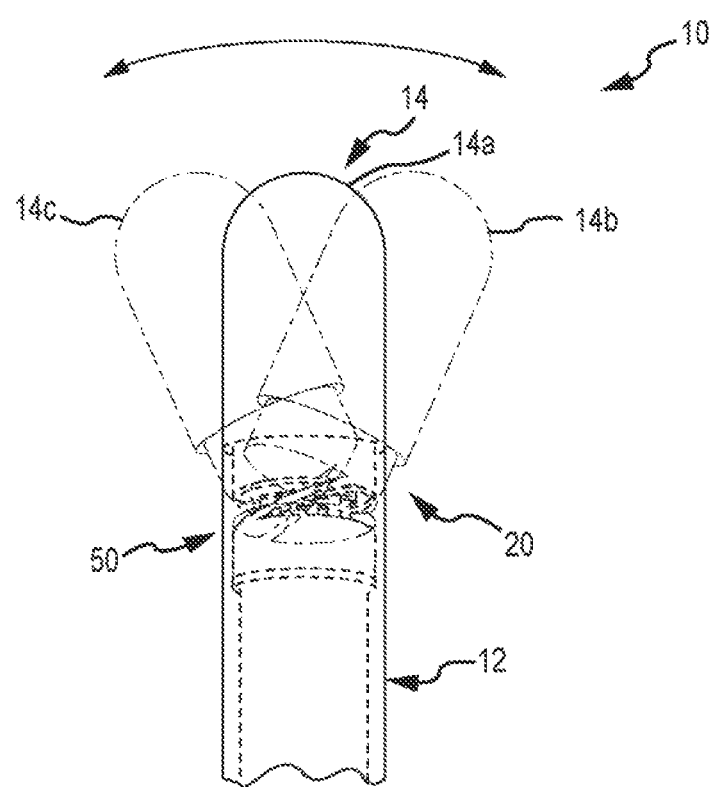
FIGS. 8A-8B are exemplary views of the coupler assembly fitted to a catheter similar to that shown in FIG. 7B illustrating movement of the coupler assembly relative to the catheter.
Figure 8B:
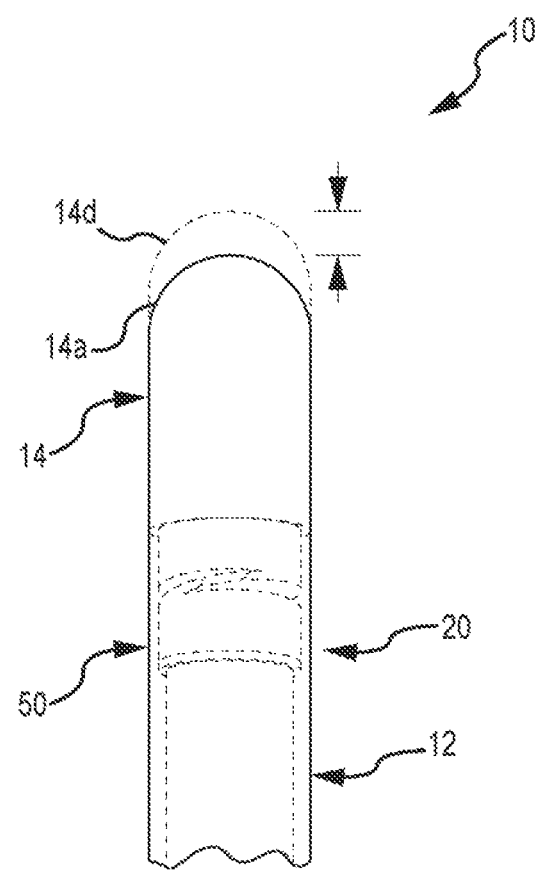

As generally illustrated in FIGS. 1 and 2, base portion 26 of electrode 14 is connected to the catheter 12 via the coupling member 50. As tip portion 24 of electrode 14 is exposed to external force through contact with tissue (e.g., as illustrated in FIGS. 8A-8B), the tip 24 of electrode 14 moves relative to the catheter body 18. In order to facilitate this movement (e.g., bending, rotation, and compression) of the tip portion 24 of the catheter 12 during use, catheter 12 may be fitted with a coupler assembly 50 in the distal end 20 of the catheter 12.

Figure 3:
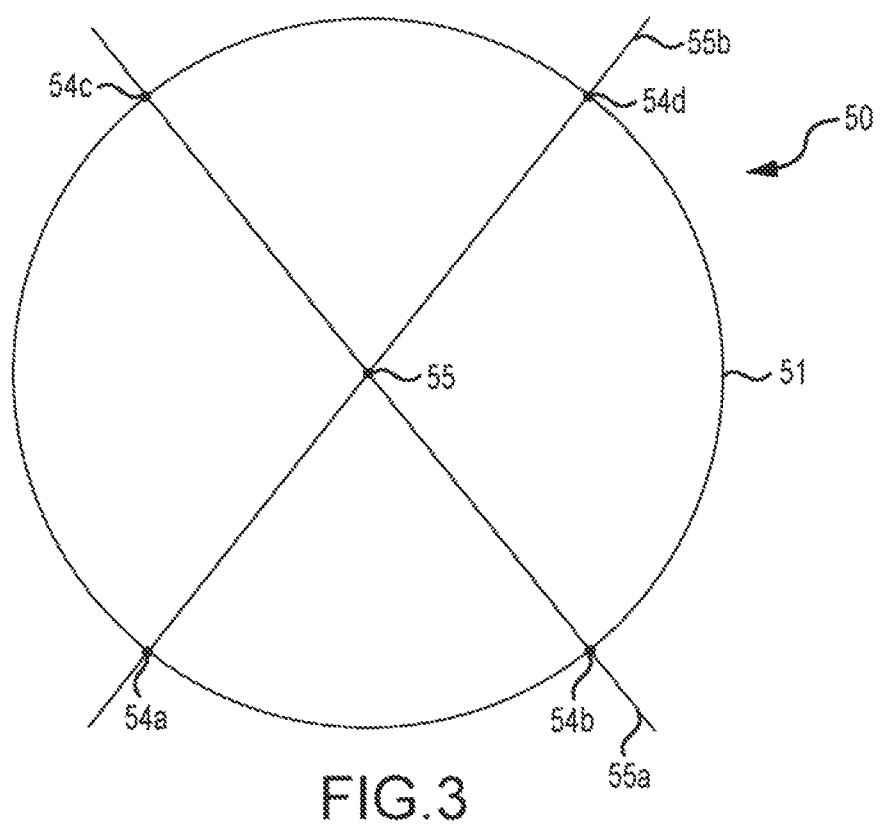
FIGS. 3 and 3A-3D show an exemplary embodiment of a coupler assembly with compliant joints according to the invention.
Figure 3A:
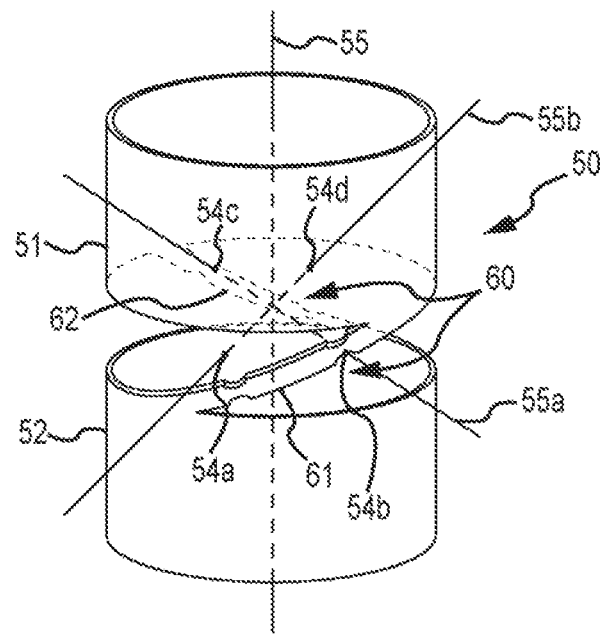

FIGS. 3 and 3A-3D show an exemplary embodiment of a coupler assembly 50 having a generally spherical operating configuration. FIG. 3 shows a top-plan view and FIGS. 3A-3D are perspective views. The coupler assembly 50 may include a first cylinder portion 51 for connecting to a structure (such as the electrode 14), and a second cylinder portion 52 for connecting to the distal end 20 of a body 18 of the catheter 12. The coupler assembly 50 also includes a spherical linkage 60 including at least two link arms 61 and 62.

Each of the two link arms 61 and 62 are connected on one end to the first cylinder portion 51 and on the other end to the second cylinder portion 52. In the embodiment shown in FIGS. 3A-3D, the link arms 61 and 62 are formed with compliant joints 54 for joining the first cylinder portion 51 to the second cylinder portion 52. Two compliant joints 54 are shown as semi-circular indentations at each end of both link arms 61 and 62. Of course other configurations for providing compliant joints are also contemplated.

The joint axes 55a and 55b of the spherical linkage intersect at the same virtual center 55. In one embodiment, the virtual center 55 may be on the axis of the catheter, although any suitable axes may be used. Additionally, the virtual center 55 may be anywhere along the axis. It is also noted that the angle formed between axes 55a and 55b may be 90 degrees or any other suitable angle. Selection of the position of virtual center 55 and the angle between axes 55a and 55b may depend at least in part on design considerations.

The distal end rotates about this virtual center 55 such that when a force is applied to the first cylindrical portion 51 or a structure (such as the electrode 14) connected to the first cylindrical portion 51 the resulting angular displacement is substantially equally responsive to forces in the x-y plane. The force in z-direction is taken up by the flexure in the mechanism. Thus, this coupler separates forces in the transverse and axial direction. The applied force can then be correlated and calibrated with the angular displacement. Conversely, the calibrated angular displacement may be used to determine the applied force.

Furthermore, when a force is applied in the longitudinal or axial (z) direction to the first cylindrical portion 51 or a structure (such as the electrode 14) connected to the first cylindrical portion 51, the spherical linkage and the compliance of the linkage (either in the joints or in the link itself) in the axial (z) direction causes displacement along the axial (z) direction. This allows a compliance or a force/displacement sensor that can measure force given rotation about two axes, such as the transverse axes (x, y) and displacement along one axis such as the longitudinal axis (z). Thus, this embodiment provides a compact design of three degrees-of-freedom force/displacement sensor in a very compact design. Such a sensor could be interchangeably used to determine displacement from a measured force. Additionally, this design allows for the links to be confined to the peripheral solid portion of the cylinder and not interfere with the space within the catheter thereby leaving room for other components and other devices within the catheter.

It will be understood by one of skill in this art that other joints may be substituted for the revolute and compliant joints described here to obtain similar effects including sliders and cams.

The coupler assembly 50 may be manufactured as a single component. In an exemplary embodiment, a cylindrical section of tubing may be cut (e.g., using a laser for microprecision) in a threaded or "corkscrew" configuration, such that the cut tubing forms opposing cylinder portions 51 and 52 connected to one another by link arms 61 and 62.

The spherical linkage may be manufactured of a variety of different materials to provide for different elastic properties based on specific catheter uses. The coupler assembly 50 and components thereof may be designed so that the movement of an electrode 14 attached to the coupler assembly 50 has a uniform response in the generally x, y and z directions of a force and/or torque applied to the electrode for measurement by the contact sensing assemblies disclosed herein.

Figure 3B:
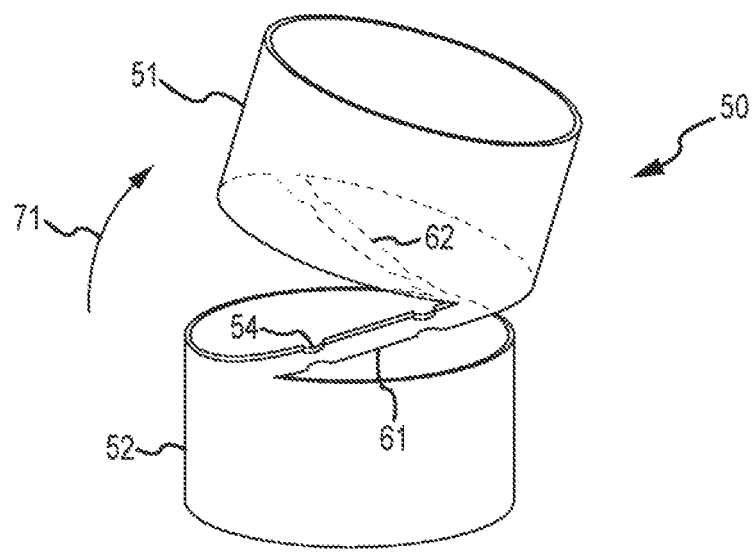
Figure 3C:
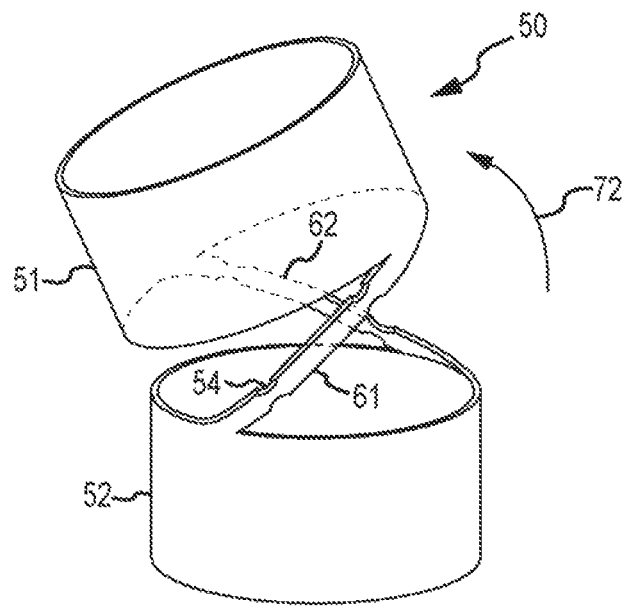
Figure 3D:
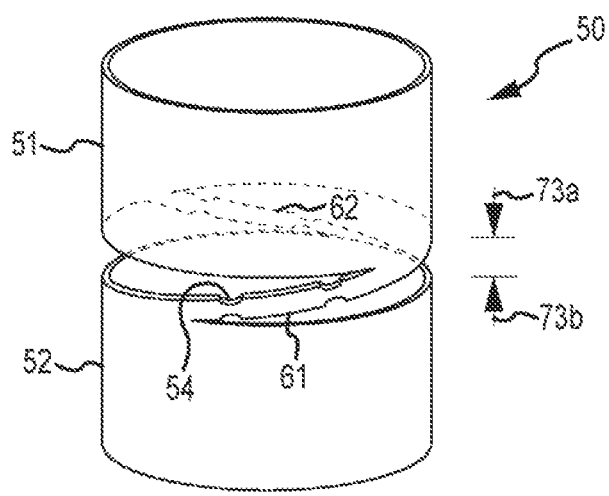
Figure 4A:
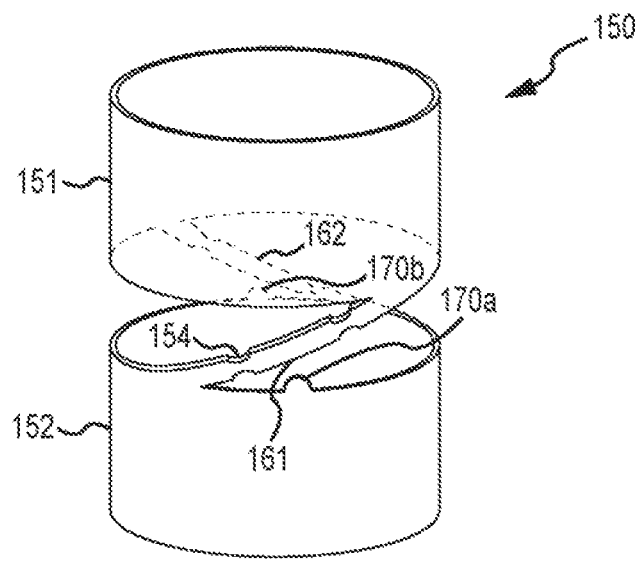
FIGS. 4A-4D show an alternative exemplary embodiment of a coupler assembly similar to that shown in FIGS. 3A-3D, wherein the coupler assembly includes a stop surface and a displacement stop.
Figure 4B:
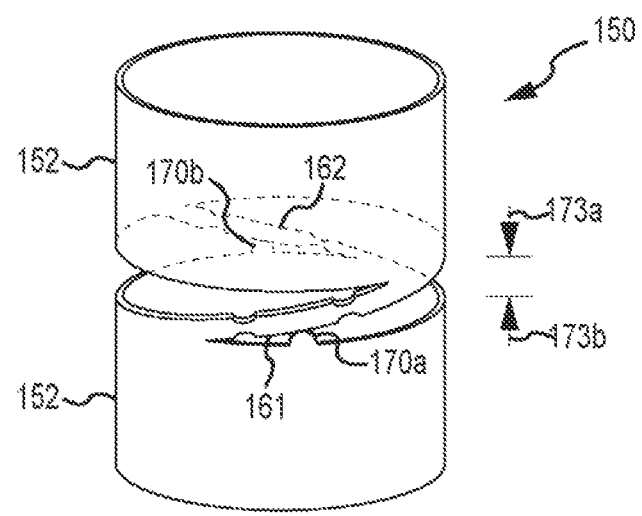
Figure 4C:
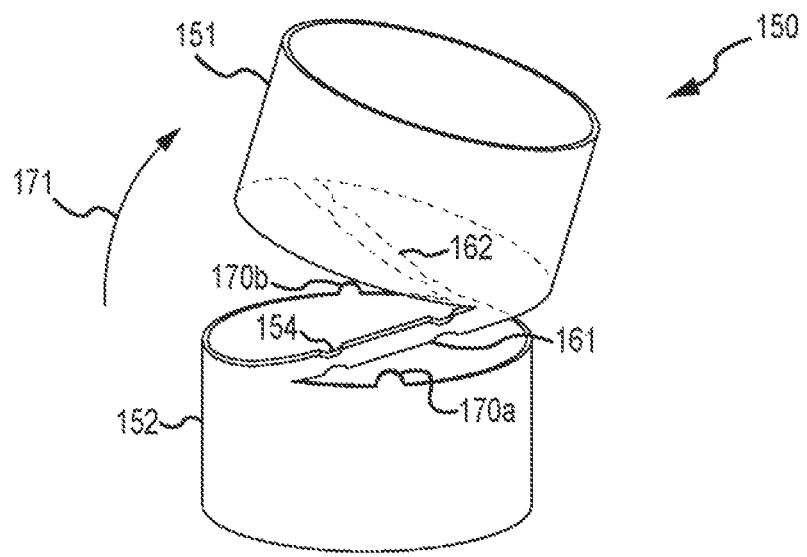
Figure 4D:
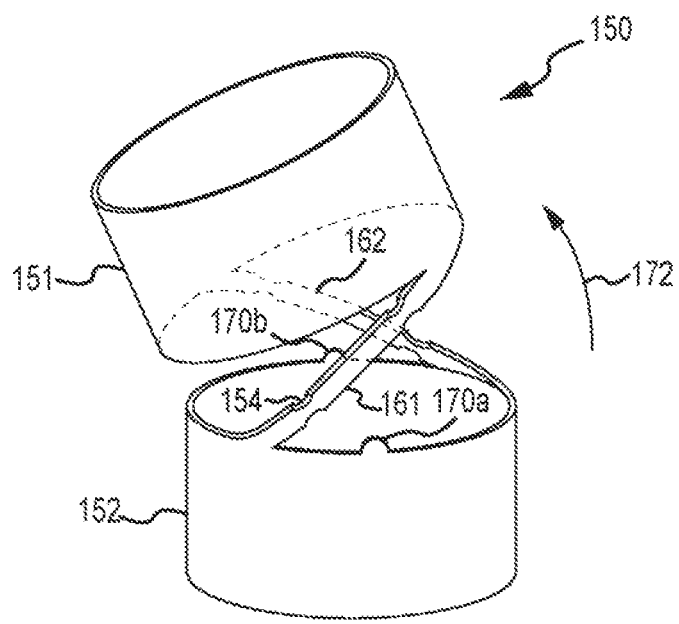

It can readily be seen in FIGS. 3B-3D how the spherical operating configuration of the coupler assembly 50 enables motion about the rotational axis such that the motion in the transverse direction (x, y) is controlled by the spherical mechanism and the translation in the axial direction (z) depends on the compliance of the coupler and the clearance in the linkage. Accordingly, the coupler assembly 50 enables controlled movement in response to external bending or rotational pressure on one of the cylinder portions, e.g., as illustrated by arrow 71 in FIG. 3B and arrow 72 in FIG. 3C. The coupler assembly 50 is also responsive to external compressive pressure, e.g., as illustrated by arrows 73a-b in FIG. 3D. In each of these figures, motion of the first cylinder portion 51 is shown relative to the second cylinder portion 52.

FIGS. 4A-4D show an alternative exemplary embodiment of a coupler assembly 150 similar to that shown in FIGS. 3A-3D. It is noted that 100-series reference numbers identify similar components to those already described above for FIGS. 3A-3D and therefore may not be described again with reference to FIGS. 4A-D for sake of clarity.

The coupler assembly 150 includes a displacement stop 170a and 170b for each link arm 161 and 162, respectively. In operation, the displacement stops 170a and 170b cooperates with a stop surface (e.g., on the link arm 161 and 162, respectively) to limit compression of the electrode 14 in a direction toward the catheter 12, as illustrated by arrows 173a and 173b, and controls or limits the stress of the arms in this configuration. It can be seen in FIGS. 4C-4D, however, that the displacement stops 170a and 170b do not interfere with or otherwise limit rotational movement of the electrode 14, as illustrated by arrow 171 in FIG. 4C and arrow 172 in FIG. 4D.

Figure 5:
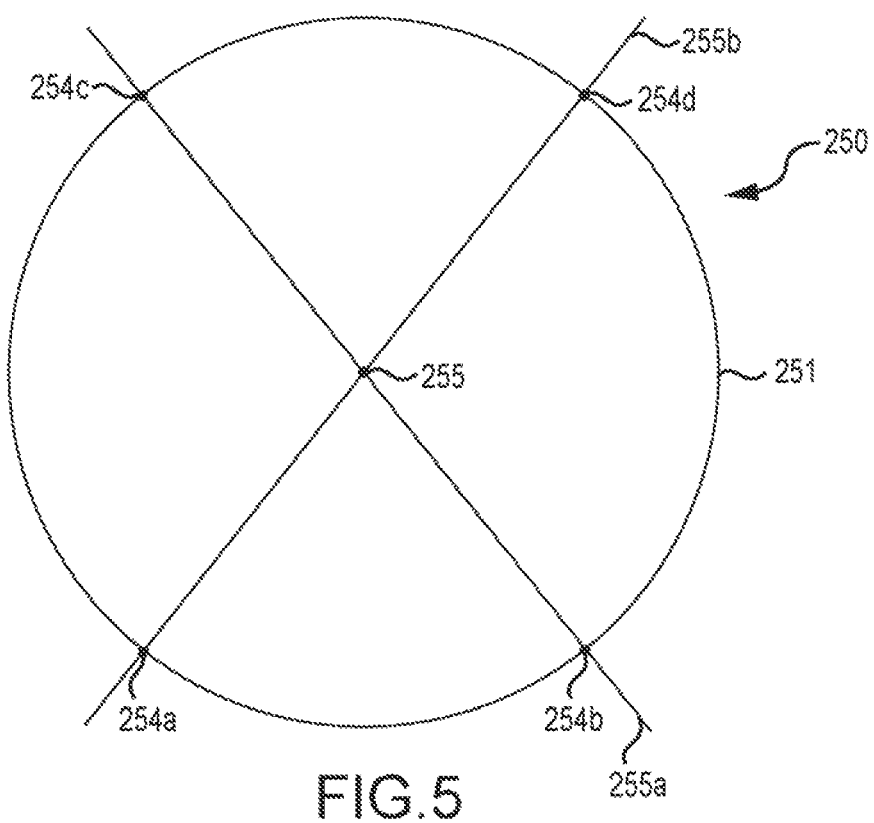
FIGS. 5 and 5A-5D show an alternative exemplary embodiment of a coupler assembly with revolute joints according to the invention.
Figure 5A:
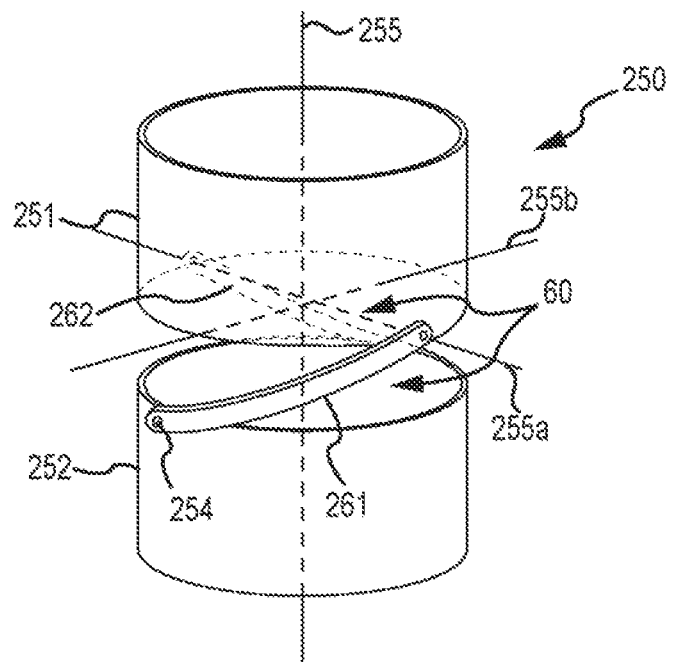

FIGS. 5 and 5A-5D show an alternative exemplary embodiment of a coupler assembly 250 according to the invention, similar to that shown in FIGS. 3 and 3A-3D but having revolute joints instead of compliant joints. Again, FIG. 5 shows a top-plan view and FIGS. 5A-5D are perspective views. It is noted that 200-series reference numbers identify similar components to those already described above for FIGS. 3A-3D and therefore may not be described again with reference to FIGS. 5A-D for sake of clarity.

The coupler assembly 250 again includes a first cylinder portion 251 for connecting to a structure (such as the electrode 14), and a second cylinder portion 252 for connecting to the distal end 20 of a body 18 of the catheter 12. The coupler assembly 250 also includes a spherical linkage 260 including at least two link arms 261 and 262.

Each of the two link arms 261 and 262 are connected on one end to the first cylinder portion 251 and on the other end to the second cylinder portion 252. In the embodiment of the coupler assembly 250 shown in FIGS. 5A-5D, however, the link arms 261 and 262 are attached with revolute joints 254 (e.g., pins) for joining the first cylinder portion 251 to the second cylinder portion 252. In this embodiment, the coupler assembly 250 is manufactured from multiple, separate components.

The joint axes 255a and 255b of the spherical linkage intersect at the same virtual center 255. In one embodiment, the virtual center 255 may be on the axis of the catheter, although any suitable axes may be used. Additionally, the virtual center 255 may be anywhere along the axis. It is also noted that the angle formed between axes 255a and 255b may be 90 degrees or any other suitable angle based. Selection of the position of virtual center 255 and the angle between axes 255a and 255b may depend at least in part on design considerations.

The distal end rotates about this virtual center 255 such that when a force is applied to the first cylindrical portion 251 or a structure (such as the electrode 14) connected to the first cylindrical portion 251 the resulting angular displacement is substantially equally responsive to forces in the x-y plane. The force in z-direction is taken up by the flexure in the mechanism. Thus, this coupler separates forces in the transverse and axial direction. The applied force can then be correlated and calibrated with the angular displacement. Conversely, the calibrated angular displacement may be used to determine the applied force.

Figure 5B:
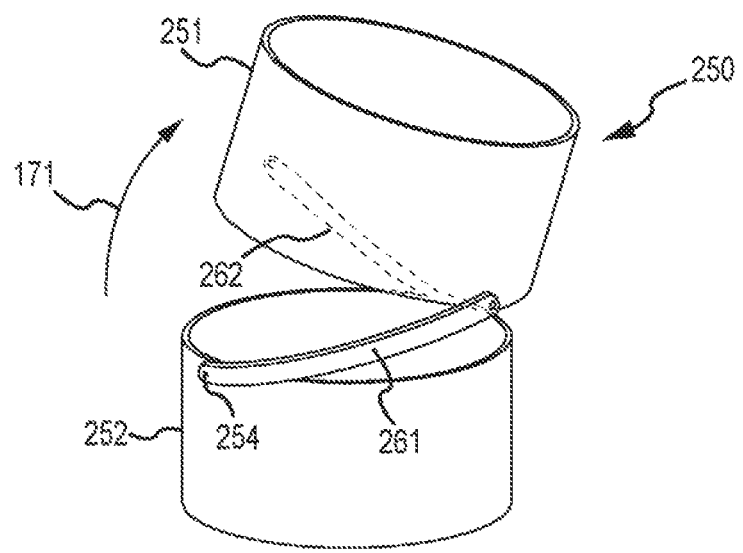
Figure 5C:
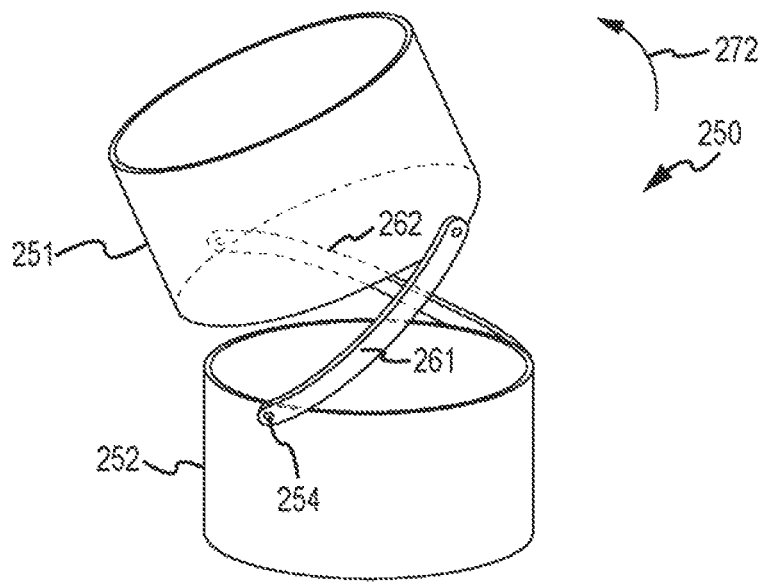
Figure 5D:
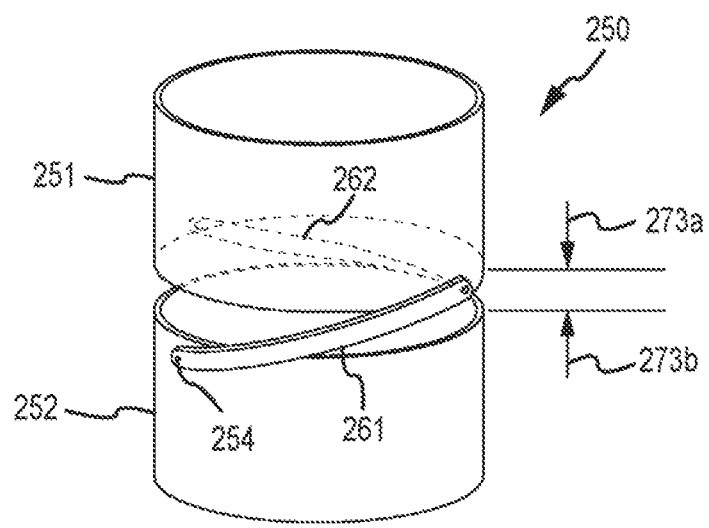

It can readily be seen in FIGS. 5B-5D how the spherical operating configuration of the coupler assembly 250 with revolute joints also enables motion about the rotational axis such that the motion in the transverse direction (x, y) is controlled by the spherical mechanism and the translation in the axial direction (z) depends on the compliance of the coupler and the clearance in the linkage. Accordingly, the coupler assembly 250 enables controlled movement in response to external bending or rotational pressure on one of the cylinder portions, e.g., as illustrated by arrow 271 in FIG. 5B and arrow 272 in FIG. 5C. The coupler assembly 250 is also responsive to external compressive pressure, e.g., as illustrated by arrows 273a-b in FIG. 5D. In each of these figures, motion of the first cylinder portion 251 is shown relative to the second cylinder portion 252.

Figure 5E:
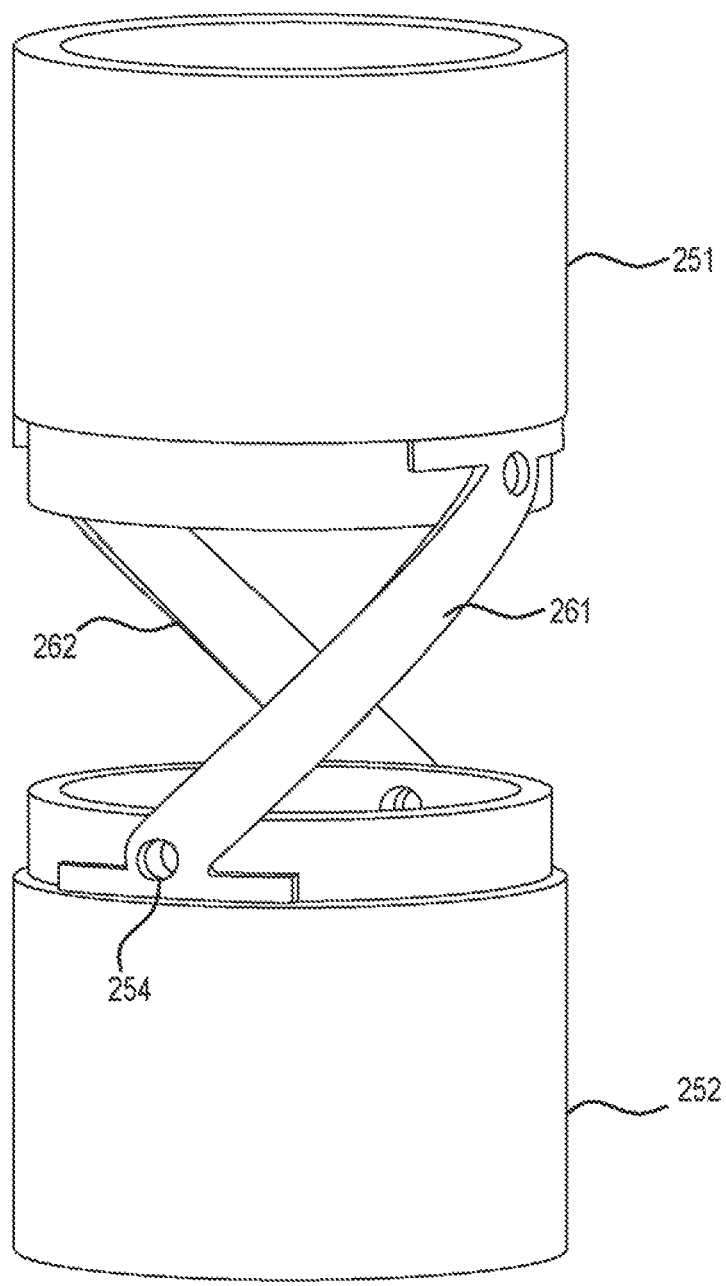
FIG. 5E shows an alternative exemplary embodiment of a coupler assembly according to the invention, similar to that shown in FIGS. 5A-5D but having a lip and stopper to form a "leaf spring" type configuration.
Figure 6A:
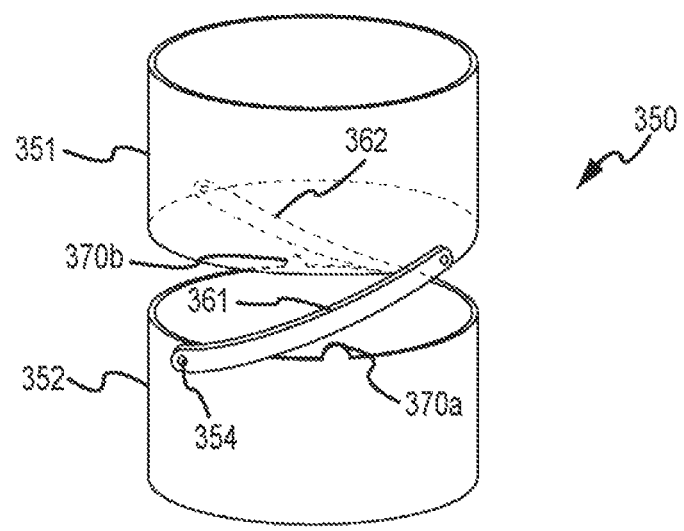
FIGS. 6A-6D show an alternative exemplary embodiment of a coupler assembly similar to that shown in FIGS. 5A-5D, wherein the coupler assembly includes a stop surface and a displacement stop.
Figure 6B:
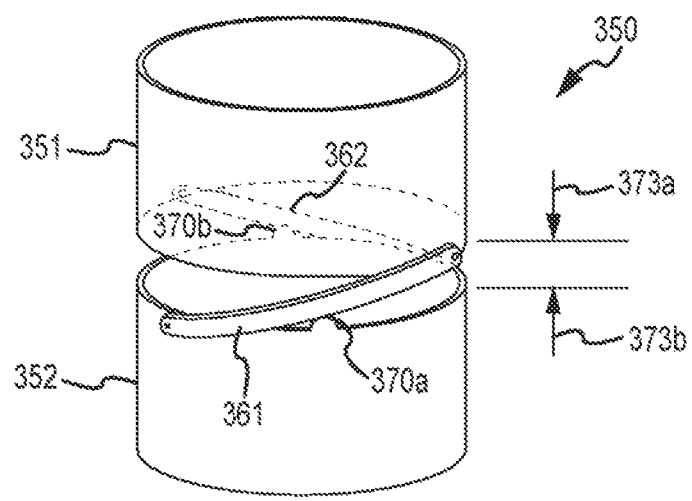
Figure 6C:
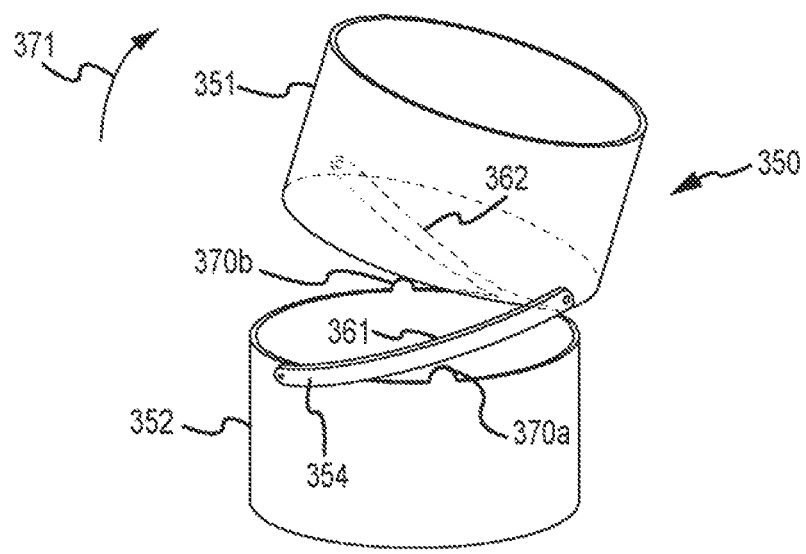
Figure 6D:
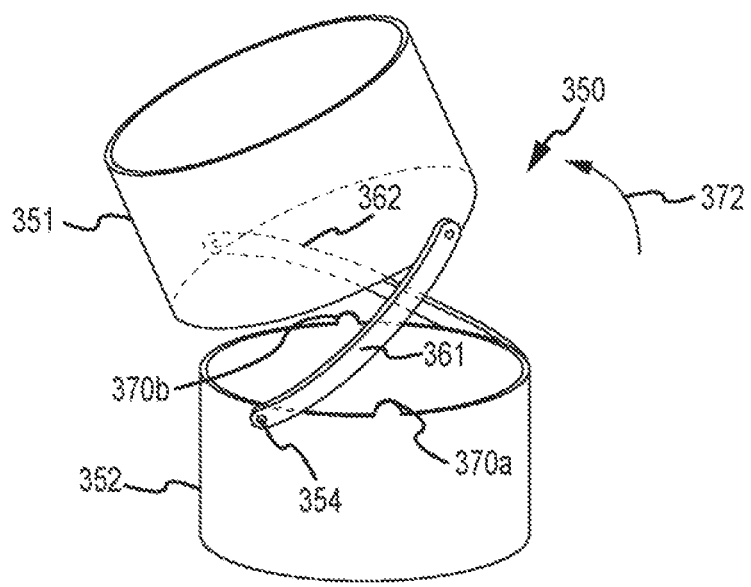

FIG. 5E shows an alternative exemplary embodiment of a coupler assembly according to the invention, similar to that shown in FIGS. 5A-5D but having a lip and stopper to form a "leaf spring" type configuration. Such an embodiment aids in the elasticity of the joints and allows the joints to readily spring back to a preconfigured orientation.

FIGS. 6A-6D show an alternative exemplary embodiment of a coupler assembly similar to that shown in FIGS. 5A-5D, wherein the coupler assembly includes a stop surface and a displacement stop. It is noted that 300-series reference numbers identify similar components to those already described above for FIGS. 3A-3D and therefore may not be described again with reference to FIGS. 6A-D for sake of clarity.

The coupler assembly 350 includes a displacement stop 370a and 370b for each link arm 361 and 362, respectively. In operation, the displacement stops 370a and 370b cooperates with a stop surface (e.g., on the link arm 361 and 362, respectively) to limit compression of the electrode 14 in a direction toward the catheter 12, as illustrated by arrows 373a and 373b. It can be seen in FIGS. 6C-6D, however, that the displacement stops 370a and 370b do not interfere with or otherwise limit rotational movement of the electrode 14, as illustrated by arrow 371 in FIG. 6C and arrow 372 in FIG. 6D.

Figure 7A:
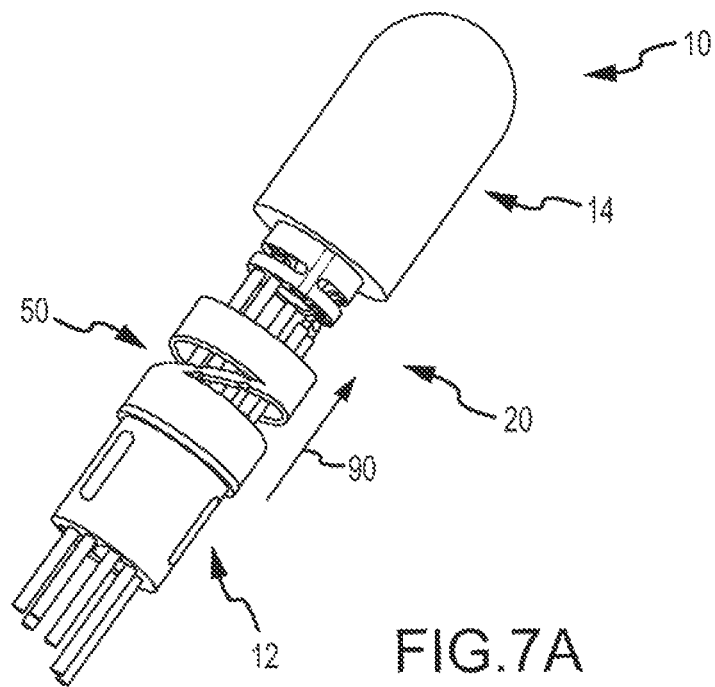
FIGS. 7A-7B are exemplary views of the coupler assembly similar to that shown in FIGS. 3A-3D as the coupler assembly may be fitted to a catheter.
Figure 7B:
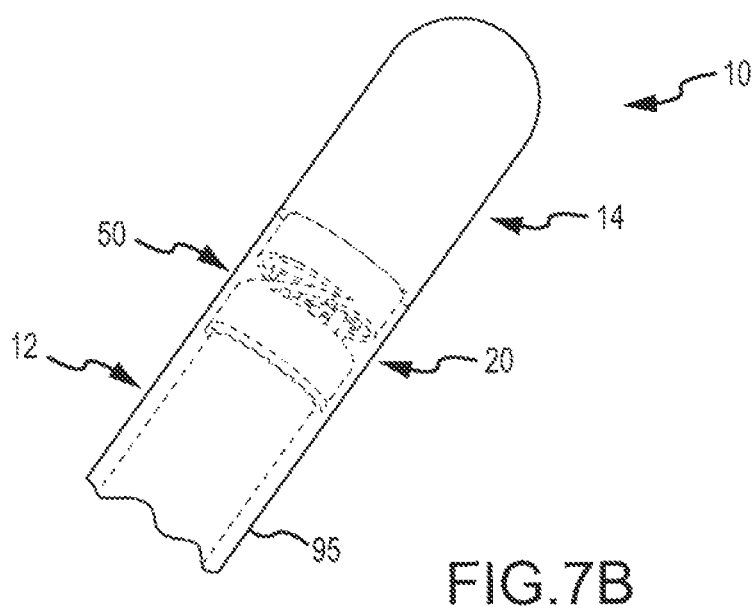

FIGS. 7A-7B are exemplary views of the coupler assembly similar to that shown in FIGS. 3A-3D as the coupler assembly 50 may be fitted to a catheter. For example, the coupler assembly 50 may be connected on the base or second cylinder portion 52 to the catheter 12 (e.g., by threading, snap, or other connection) and moved in the direction of arrow 90 into connection with the electrode 14 (e.g., again by threading, snap, or other connection). A catheter tubing or sheath 95 may then be slid over the internal components of the catheter 12 and the coupler assembly 50.

FIGS. 8A-8B are exemplary views of the coupler assembly fitted to a catheter similar to that shown in FIG. 7B illustrating movement of the coupler assembly relative to the catheter. In operation, with coupler assembly 50 installed onto a base portion of the electrode 14, any axial, transverse or otherwise rotational forces, and/or compressive forces applied to electrode 14 when contacting a membrane or other surface may result in controlled deformation of portion 20 of the catheter 12. The resulting deformation may directly correlate to the axial, transverse or otherwise rotational forces applied to electrode 14, with the forces and angle of rotation being calculated depending on the type of sensor being implemented.

The invention further contemplates use of the catheter 12 with a system that includes assembly 10 of the invention connected to a signal converter (not shown), such as an analog to digital converter or other suitable signal processing capability, and an operator interface, which may further include a computer and display (also not shown), for processing the signals received from assembly 10 in connection with positioning and contact with tissue, such as myocardial tissue. This information is processed to determine the contact force exerted on electrode 14 of assembly 10. A calibration system (not shown), e.g., implemented in software, may be further provided to correlate the amplitude or intensity of the received signal to the external force on the electrode. A mapping system, such as the Ensite system, also known as NavX®, may be integrated with the system to provide a visualization and mapping system for use in connection with assembly 10 of the invention. In an alternate embodiment, the signal processor may be integrated with each of the receivers provided by the sensor(s), such that the signal is directly processed and provided on the operator interface. Overall, each of these components may be modified and/or integrated with one another depending on the design of the optical system as recognized by one of ordinary skill in the art.

As previously described, the invention provides a method of sensing contact force and/or orientation as provided by the contact sensing assembly and system. The signals may be correlated to, among other things, force vectors exerted by the electrode on an adjacent tissue.

EXAMPLES

The following are examples of other embodiments which are contemplated, and are provided for purposes of illustration, but are not intended to be limiting in any manner.

A spherical linkage coupler for a catheter, comprising: a first cylinder portion for connecting to a structure; a second cylinder portion for connecting to a distal end of a body of the catheter; a spherical linkage including at least two link arms, wherein each of the at least two link arms is connected on one end to the first cylinder portion and on the other end to the second cylinder portion, thereby connecting a portion of the structure to the distal end of the catheter and enabling the structure to move relative to the distal end of the catheter in response to an external force exerted on the structure.

The coupler, wherein the spherical linkage is configured to enable rotation of the structure relative to the body of the catheter.

The coupler, wherein the spherical linkage is configured to enable compression of the structure toward the body of the catheter.

The coupler, wherein the at least two link arms are connected to the first and second cylinder portions by revolute joints.

The coupler, wherein the at least two link arms are connected to the first and second cylinder portions by compliant joints.

The coupler, further comprising: at least one stop surface; and at least one displacement stop, the displacement stop cooperating with the stop surface to limit compression of the structure toward the body of the catheter.

The coupler, wherein the at least two link arms include compliant joints.

The coupler, wherein at least one sensor is operatively connected to one of the structure and the catheter body.

The coupler, wherein the spherical linkage is configured to enable external axial and transverse forces and torques exerted on the structure to be sensed by the at least one sensor.

A method for sensing contact force in a catheter, comprising: connecting a first cylinder portion to a structure; connecting a second cylinder portion to a distal end of a body of the catheter; providing a spherical linkage to connect the first cylinder portion to the second cylinder portion so that the structure moves relative to the distal end of the body of the catheter in response to an external force exerted on the structure; providing a sensor for the structure.

The method, wherein the structure senses changes in intensity of a signal from the sensor responsive to displacement associated with the structure in response to the contact force exerted by the structure on a tissue.

The method, wherein the structure performs one of RF ablation, HIFU ablation, laser ablation, cryogenic ablation, chemical ablation, radiation therapy, ultrasonic imaging, electrical pacing, EP pacing, electrical sensing, and EP sensing.

The method, further comprising determining the axial and transverse components of contact force as a function of an angle of attack of the structure relative to the tissue.

The method, further comprising using a calibrated sensor to determine axial and transverse components of the contact force.

The method, further comprising determining the contact force magnitude as a function of the axial and transverse components of the contact force.

The method, further comprising determining an angle of attack of the structure relative to the tissue as a function of the axial and transverse components of the contact force.

The method, further comprising determining an angle of rotation of the structure relative to the tissue as a function of the change in intensity and phase angle of the sensor.

Although a number of embodiments of this invention have been described above with a certain degree of particularity, those skilled in the art could make numerous alterations to the disclosed embodiments without departing from the spirit or scope of this invention. For example, all joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An elongate medical device assembly comprising:
   a distal portion;
   a proximal portion;
   a coupler assembly connecting the distal portion to the proximal portion, the coupler assembly comprising:
      a first cylinder portion coupled with the proximal portion and having a circumference and a second cylinder portion coupled with the distal portion; and
      two link arms, each connected on one end to the first cylinder portion and on the other end to the second cylinder portion and extending circumferentially around less than the entire circumference, wherein the coupler assembly is configured to enable compression of the distal tubular portion towards the proximal tubular portion; and
   a sensor, coupled with at least one of the distal tubular portion and the proximal tubular portion, configured to detect the compression.

2. The elongate medical device assembly of claim 1, wherein the sensor comprises an optical sensor.

3. The elongate medical device assembly of claim 2, wherein the optical sensor comprises an emitter and a receiver, the emitter configured to emit an optical signal between the distal portion and the proximal portion.

4. The elongate medical device assembly of claim 3, further comprising an optically interactive surface configured to reflect the optical signal from the emitter to the receiver.

5. The elongate medical device assembly of claim 4, wherein the optically interactive surface is stationary relative to the distal portion.

6. The elongate medical device assembly of claim 1, wherein the distal portion comprises a portion of a tip electrode.

7. The elongate medical device assembly of claim 1, wherein the proximal portion comprises an elongate flexible body.

8. The elongate medical device assembly of claim 1, wherein the coupler assembly is configured to enable circumferential rotation of the distal portion relative to the proximal portion.

9. The elongate medical device assembly of claim 8, wherein the sensor is configured to detect the rotation.

10. A catheter assembly comprising:
    an electrode;
    an elongate flexible body;
    a coupler assembly comprising:
       a first cylinder portion coupled with the elongate flexible body and having a circumference and a second cylinder portion coupled with the electrode; and
       two link arms, each connected on one end to the first cylinder portion and on the other end to the second cylinder portion and extending circumferentially around less than the entire circumference, wherein the coupler assembly is configured to enable compression of the electrode towards the elongate flexible body; and a sensor, coupled with at least one of the electrode and the elongate flexible body, configured to detect the compression.

11. The catheter assembly of claim 10, wherein the electrode comprises a tip electrode.

12. The catheter assembly of claim 10, wherein the sensor comprises an optical sensor.

13. The catheter assembly of claim 12, wherein the optical sensor is coupled with an optical fiber that extends longitudinally through the elongate flexible body.

14. The catheter assembly of claim 12, wherein the optical sensor comprises an emitter and a receiver disposed within a single optical fiber.

15. The catheter assembly of claim 10, wherein a portion of the sensor is stationary relative to the first cylinder portion.

16. The catheter assembly of claim 10, wherein a portion of the sensor is stationary relative to the elongate body.

17. The catheter assembly of claim 10, wherein a portion of the sensor is moveable relative to the electrode.

18. The catheter assembly of claim 10, wherein a portion of the sensor is moveable relative to the second cylinder portion.

19. The catheter assembly of claim 10, wherein the coupler assembly is configured to enable circumferential rotation of the electrode relative to the elongate body.

20. The elongate medical device assembly of claim 19, wherein the sensor is configured to detect the rotation.

* * * * *